US008350098B2

(12) United States Patent
Johnston et al.

(10) Patent No.: US 8,350,098 B2
(45) Date of Patent: Jan. 8, 2013

(54) ETHANOL PRODUCTION FROM ACETIC ACID UTILIZING A MOLYBDENUM CARBIDE CATALYST

(75) Inventors: Victor J. Johnston, Houston, TX (US); Barbara F. Kimmich, Bernardsville, NJ (US); Jan Cornelis van der Waal, Delft (NL); James H. Zink, League City, TX (US); Virginie Zuzaniuk, Krommenie (NL); Josefina T. Chapman, Houston, TX (US); Laiyuan Chen, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 36 days.

(21) Appl. No.: 13/079,684

(22) Filed: Apr. 4, 2011

(65) Prior Publication Data
US 2012/0253085 A1    Oct. 4, 2012

(51) Int. Cl.
*C07C 29/149* (2006.01)
(52) U.S. Cl. ...................................... 568/885
(58) Field of Classification Search ............... 568/885
See application file for complete search history.

(56) References Cited

U.S. PATENT DOCUMENTS

| | | |
|---|---|---|
| 2,021,698 A | 11/1935 | Perkins |
| 2,105,540 A | 1/1938 | Lazier |
| 2,136,704 A | 11/1938 | Mitchell |
| 2,607,807 A | 8/1952 | Ford |
| 2,744,939 A | 5/1956 | Kennel |
| 2,882,244 A | 4/1959 | Milton |
| 3,130,007 A | 4/1964 | Breck |
| 3,478,112 A | 11/1969 | Adam |
| 3,702,886 A | 11/1972 | Araguer |
| 3,729,429 A | 4/1973 | Robson |
| 3,990,952 A | 11/1976 | Katzen |
| 4,065,512 A | 12/1977 | Cares |
| 4,228,307 A | 10/1980 | Zimmerschied |
| 4,270,015 A | 5/1981 | Knifton |
| 4,275,228 A | 6/1981 | Gruffaz |
| 4,317,918 A | 3/1982 | Takano |
| 4,328,373 A | 5/1982 | Strojny |
| 4,337,351 A | 6/1982 | Larkins, Jr. |
| 4,374,265 A | 2/1983 | Larkins, Jr. |
| 4,395,576 A | 7/1983 | Kwantes |
| 4,398,039 A | 8/1983 | Pesa |
| 4,399,305 A | 8/1983 | Schreck |
| 4,421,939 A | 12/1983 | Kiff |
| 4,443,639 A | 4/1984 | Pesa |
| 4,465,854 A | 8/1984 | Pond |
| 4,471,136 A | 9/1984 | Larkins |
| 4,480,115 A | 10/1984 | McGinnis |
| 4,517,391 A | 5/1985 | Schuster |
| 4,521,630 A | 6/1985 | Wattimena |
| 4,550,185 A | 10/1985 | Mabry |
| 4,581,473 A | 4/1986 | Polichnowski |
| 4,613,700 A | 9/1986 | Maki |
| 4,620,050 A | 10/1986 | Cognion |
| 4,678,543 A | 7/1987 | Houben |
| 4,692,218 A | 9/1987 | Houben |
| 4,777,303 A | 10/1988 | Kitson |
| 4,804,791 A | 2/1989 | Kitson |
| 4,826,795 A | 5/1989 | Kitson |
| 4,843,170 A | 6/1989 | Isshiki |
| 4,886,905 A | 12/1989 | Larkins, Jr. |
| 4,902,823 A | 2/1990 | Wunder |
| 4,978,778 A | 12/1990 | Isshiki |
| 4,985,572 A | 1/1991 | Kitson |
| 4,990,655 A | 2/1991 | Kitson |
| 5,008,235 A | 4/1991 | Wegman |
| 5,061,671 A | 10/1991 | Kitson |
| 5,124,004 A | 6/1992 | Grethlein |
| 5,137,861 A | 8/1992 | Shih |
| 5,149,680 A | 9/1992 | Kitson |
| 5,155,084 A | 10/1992 | Horn |
| 5,185,308 A | 2/1993 | Bartley |
| 5,241,106 A | 8/1993 | Inoue |
| 5,243,095 A | 9/1993 | Roberts |
| 5,306,845 A | 4/1994 | Yokohama |
| 5,350,504 A | 9/1994 | Dessau |
| 5,426,246 A | 6/1995 | Nagahara |
| 5,475,144 A | 12/1995 | Watson |
| 5,476,827 A | 12/1995 | Ferrero |
| RE35,377 E | 11/1996 | Steinberg |
| 5,585,523 A | 12/1996 | Weiguny |
| 5,691,267 A | 11/1997 | Nicolau |
| 5,719,315 A | 2/1998 | Tustin |
| 5,731,456 A | 3/1998 | Tustin |
| 5,767,307 A | 6/1998 | Ramprasad |
| 5,821,111 A | 10/1998 | Grady |

(Continued)

FOREIGN PATENT DOCUMENTS

EP        0104197        4/1984
(Continued)

OTHER PUBLICATIONS

International Search Report and Written Opinion mailed May 22, 2012 in corresponding International Application No. PCT/US2012/031207.
Minglin Xiang et al., "XPS study of potassium-promoted molybdenum carbides for mixed alcohols synthesis via CO hydrogenation", Journal of Natural Gas Chemistry, vol. 19, 2010, pp. 151-155.
P. Da Costa et al., "05/00048 Deep hydrodesulphurization and hydrogenation of diesel fuels on alumina-supported and bulk molybdenum carbide catalysts", Fuel and Energy Abstracts, Elsevier, vol. 46, No. 1, Jan. 1, 2005, XP 027760839, p. 8.
Alcala, et al., (2005). Experimental and DFT studies of the conversion of ethanol and acetic acid on PtSn-based catalysts, Journal of Physical Chemistry, 109(6), 2074-2085.

(Continued)

*Primary Examiner* — Elvis O Price

(57) ABSTRACT

A process for the selective and direct formation of ethanol from acetic acid comprising contacting a feed stream containing acetic acid and hydrogen in vapor form at an elevated temperature with a hydrogenation catalyst comprising molybdenum carbide and one or more promoter metals selected from the group consisting of copper, iron, cobalt, nickel, ruthenium, rhodium, palladium, osmium, iridium, platinum, titanium, zinc, chromium, rhenium, potassium, tin and tungsten on a catalyst support.

16 Claims, No Drawings

U.S. PATENT DOCUMENTS

| | | |
|---|---|---|
| 5,849,657 A | 12/1998 | Rotgerink |
| 5,861,530 A | 1/1999 | Atkins |
| 5,945,570 A | 8/1999 | Arhancet |
| 5,955,397 A | 9/1999 | Didillon |
| 5,973,193 A | 10/1999 | Crane |
| 6,040,474 A | 3/2000 | Jobson |
| 6,049,008 A | 4/2000 | Roberts |
| 6,093,845 A | 7/2000 | van Acker |
| 6,114,571 A | 9/2000 | Abel |
| 6,121,498 A | 9/2000 | Tustin |
| 6,232,352 B1 | 5/2001 | Vidalin |
| 6,232,504 B1 | 5/2001 | Barteau |
| 6,294,703 B1 | 9/2001 | Hara |
| 6,462,231 B1 | 10/2002 | Yanagawa |
| 6,472,555 B2 | 10/2002 | Choudary |
| 6,486,366 B1 | 11/2002 | Ostgard |
| 6,495,730 B1 | 12/2002 | Konishi |
| 6,509,180 B1 | 1/2003 | Verser |
| 6,509,290 B1 | 1/2003 | Vaughn |
| 6,559,333 B1 | 5/2003 | Brunelle |
| 6,603,038 B1 | 8/2003 | Hagemeyer |
| 6,632,330 B1 | 10/2003 | Colley |
| 6,657,078 B2 | 12/2003 | Scates |
| 6,685,754 B2 | 2/2004 | Kindig |
| 6,693,213 B1 | 2/2004 | Kolena |
| 6,696,596 B1 | 2/2004 | Herzog |
| 6,727,380 B2 | 4/2004 | Ellis |
| 6,765,110 B2 | 7/2004 | Warner |
| 6,768,021 B2 | 7/2004 | Horan |
| 6,812,372 B2 | 11/2004 | Janssen |
| 6,852,877 B1 | 2/2005 | Zeyss |
| 6,903,045 B2 | 6/2005 | Zoeller |
| 6,906,228 B2 | 6/2005 | Fischer |
| 6,927,048 B2 | 8/2005 | Verser |
| 7,074,603 B2 | 7/2006 | Verser |
| 7,084,312 B1 | 8/2006 | Huber |
| 7,297,236 B1 | 11/2007 | Vander Griend |
| 7,351,559 B2 | 4/2008 | Verser |
| 7,375,049 B2 | 5/2008 | Hayes |
| 7,425,657 B1 | 9/2008 | Elliott |
| 7,507,562 B2 | 3/2009 | Verser |
| 7,518,014 B2 | 4/2009 | Kimmich |
| 7,538,060 B2 | 5/2009 | Barnicki |
| 7,553,397 B1 | 6/2009 | Colley |
| 7,572,353 B1 | 8/2009 | Vander Griend |
| 7,608,744 B1 | 10/2009 | Johnston |
| 7,863,489 B2 | 1/2011 | Johnston |
| 7,884,253 B2 | 2/2011 | Stites |
| 2003/0013908 A1 | 1/2003 | Horan |
| 2003/0077771 A1 | 4/2003 | Verser |
| 2003/0104587 A1 | 6/2003 | Verser |
| 2003/0114719 A1 | 6/2003 | Fischer |
| 2003/0191020 A1 | 10/2003 | Bharadwaj |
| 2004/0195084 A1 | 10/2004 | Hetherington |
| 2006/0019360 A1 | 1/2006 | Verser |
| 2006/0102520 A1 | 5/2006 | Lapinski |
| 2006/0106246 A1 | 5/2006 | Warner |
| 2006/0127999 A1 | 6/2006 | Verser |
| 2007/0270511 A1 | 11/2007 | Melnichuk |
| 2008/0207953 A1 | 8/2008 | Houssin |
| 2009/0005588 A1 | 1/2009 | Hassan |
| 2009/0023192 A1 | 1/2009 | Verser |
| 2009/0081749 A1 | 3/2009 | Verser |
| 2009/0166172 A1 | 7/2009 | Casey |
| 2009/0221725 A1 | 9/2009 | Chornet |
| 2009/0318573 A1 | 12/2009 | Stites |
| 2009/0326080 A1 | 12/2009 | Chornet |
| 2010/0016454 A1 | 1/2010 | Gracey |
| 2010/0029980 A1 | 2/2010 | Johnston |
| 2010/0029995 A1 | 2/2010 | Johnston |
| 2010/0029996 A1 | 2/2010 | Danjo |
| 2010/0030001 A1 | 2/2010 | Chen |
| 2010/0030002 A1 | 2/2010 | Johnston |
| 2010/0113843 A1 | 5/2010 | Lee |
| 2010/0121114 A1 | 5/2010 | Weiner |
| 2010/0168493 A1 | 7/2010 | Le Peltier |
| 2010/0196789 A1 | 8/2010 | Fisher |
| 2010/0197485 A1 | 8/2010 | Johnston |
| 2010/0249479 A1 | 9/2010 | Berg-Slot |

FOREIGN PATENT DOCUMENTS

| | | |
|---|---|---|
| EP | 0137749 | 4/1985 |
| EP | 0167300 | 1/1986 |
| EP | 0175558 | 3/1986 |
| EP | 0192587 | 8/1986 |
| EP | 0285420 | 10/1988 |
| EP | 0330853 | 8/1989 |
| EP | 0372847 | 6/1990 |
| EP | 0400904 | 12/1990 |
| EP | 0408528 | 1/1991 |
| EP | 0198682 | 3/1991 |
| EP | 0285786 | 5/1993 |
| EP | 0990638 | 4/2000 |
| EP | 1262234 | 12/2002 |
| EP | 1277826 | 1/2003 |
| EP | 2060553 | 5/2009 |
| EP | 2060555 | 5/2009 |
| EP | 2186787 | 5/2010 |
| GB | 1168785 | 10/1969 |
| GB | 1559540 | 1/1980 |
| GB | 2136704 | 9/1984 |
| JP | 4193304 | 7/1992 |
| JP | 6116182 | 4/1994 |
| JP | 10306047 | 11/1998 |
| JP | 11147845 | 6/1999 |
| JP | 2001046874 | 2/2001 |
| JP | 2001157841 | 6/2001 |
| WO | 8303409 | 10/1983 |
| WO | WO 01/28679 A1 | 4/2001 |
| WO | 03040037 | 5/2003 |
| WO | 2005102513 | 11/2005 |
| WO | 2009009322 | 1/2009 |
| WO | 2009009323 | 1/2009 |
| WO | 2009063176 | 5/2009 |
| WO | 2009086839 | 7/2009 |
| WO | 2009105860 | 9/2009 |
| WO | 2010014145 | 2/2010 |
| WO | 2010014153 | 2/2010 |
| WO | 2010055285 | 5/2010 |

OTHER PUBLICATIONS

Amit M. Goda et al., DFT modeling of selective reduction of acetic acid to acetaldehyde on Pt-based bimetallic catalysts, 20th NAM, Houston, TX, Jun. 17-22, 2007 available online at http://www.nacatsoc.org/20nam/abstracts/O-S9-18.pdf.

Brunauer Emmett and Teller, J. Am. Chem. Soc. 60, 309 (1938).

English language abstract for EP 0 137 749 A2, 1985.

English language abstract for EP 0 192 587 A1, 1986.

English language abstract for EP 0 330 853 A2, 1989.

English language abstract for JP 10-306047 A, 1998.

English language abstract for JP 11-147845 A, 1999.

English language abstract for JP 2001-046874 A, 2001.

English language abstract for JP 2001-157841 A, 2001.

English language abstract for JP 4-193304 A, 1992.

English language abstract for JP 6-116182 A, 1994.

Gursahani et al., Reaction kinetics measurements and analysis of reaction pathways for conversions of acetic acid, ethanol, and ethyl acetate over silica-supported Pt, Applied Catalysis A: General 222 (2001) 369-392.

International Preliminary Report on Patentability for PCT/US2009/004197 dated Aug. 10, 2010.

International Search Report and Written Opinion for PCT/US2009/004195 mailed Mar. 26, 2010.

International Search Report and Written Opinion for PCT/US2009/004197 mailed Mar. 24, 2010.

Ordonez et al., The role of metal and support sites on the hydrogenation of acetic acid on Ru-based catalysts, 21ST NAM San Francisco, CA, Jun. 10, 2009.

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.

Pestman et al., (1997). Reactions of Carboxylic Acids on Oxides, Journal of Catalysis 168, 255-264.

Pestman et al., (1998). Identification of the Active Sites in the Selective Hydrogenation of Acetic Acid to Acetaldehyde on Iron Oxide Catalysts, Journal of Catalysis, 174, 142-152.

Pestman et al., The formation of ketones and aldehydes from carboxylic acids, structure-activity relationship for two competitive reactions, Journal of Molecular Catalysis A: Chemical 103 Jun. 14, 1995, 175-180.

Proc. Roy Soc. A314, pp. 473-498 (1970).

Rachmady, Acetic Acid Reduction by H2 on Bimetallic Pt Fe Catalysts, Journal of Catalysis 209, 87-98 (Apr. 1, 2002), Elsevier Science (USA).

Santori et al. (2000). Hydrogenation of carbonylic compounds on Pt/SiO2 catalysts modified with SnBu4, Studies in Surface Science and Catalysis, 130, 2063-2068.

Spivey et al., "Heterogeneous catalytic synthesis of ethanol from biomass-dervied syngas," Chemical Society Review, 2007, vol. 36, pp. 1514-1528.

Subramani et al., "A Review of Recent Literature to Search for an Efficient Catalytic Process for the Conversion of Syngas to Ethanol," Energy & Fuels, 2008, vol. 22, pp. 814-839.

ZeaChem, Inc., Technology Overview, Lakewood, Colorado www.zeachem.com, 2008.

Zheng, et al. (2007). Preparation and catalytic properties of a bimetallic Sn-Pt complex in the supercages of NaY zeolite by use of surface organometallic chemistry, Applied Organometallic Chemistry, 21(10), 836-840.

ETHANOL PRODUCTION FROM ACETIC ACID UTILIZING A MOLYBDENUM CARBIDE CATALYST

FIELD OF THE INVENTION

The present invention relates generally to a process for the selective and direct formation of ethanol from acetic acid utilizing a catalyst comprising molybdenum carbide and one or more promoter metals selected from the group consisting of copper, iron, cobalt, nickel, ruthenium, rhodium, palladium, osmium, iridium, platinum, titanium, zinc, chromium, rhenium, potassium, tin and tungsten, supported on a catalyst support.

BACKGROUND OF THE INVENTION

There is a long felt need for an economically viable process to convert acetic acid to ethanol. Ethanol is an important commodity feedstock for a variety of industrial products and is also used as a fuel additive with gasoline. Ethanol can readily be dehydrated to ethylene, which can then be converted to a variety of products, both polymeric and small molecule-based. Ethanol is conventionally produced from feedstocks where price fluctuations are becoming more significant. That is, fluctuating natural gas and crude oil prices contribute to fluctuations in the cost of conventionally produced, petroleum, natural gas or corn or other agricultural product-sourced ethanol, making the need for alternative sources of ethanol all the greater when oil prices and/or agricultural product prices rise.

It has been reported that ethanol can be produced from the hydrogenation of acetic acid, but most of these processes feature several drawbacks for a commercial operation. For instance, U.S. Pat. No. 2,607,807 discloses that ethanol can be formed from acetic acid over a ruthenium catalyst at extremely high pressures of 700-950 bars in order to achieve yields of around 88%, whereas low yields of only about 40% are obtained at pressures of about 200 bar. Nevertheless, both of these conditions are unacceptable and uneconomical for a commercial operation.

More recently, it has been reported that ethanol can be produced from hydrogenating acetic acid using a cobalt catalyst again at superatmospheric pressures such as about 40 to 120 bar. See, for example, U.S. Pat. No. 4,517,391. However, the only example disclosed therein employs reaction pressure in the range of about 300 bar still making this process undesirable for a commercial operation. In addition, the process calls for a catalyst containing no less than 50 percent cobalt by weight plus one or more members selected from the group consisting of copper, manganese, molybdenum, chromium, and phosphoric acid, thus rendering the process economically non-viable. Although there is a disclosure of use of simple inert catalyst carriers to support the catalyst materials, there is no specific example of supported metal catalysts.

U.S. Pat. No. 5,149,680 describes a process for the catalytic hydrogenation of carboxylic acids and their anhydrides to alcohols and/or esters utilizing a platinum group metal alloy catalysts. The catalyst is comprised of an alloy of at least one noble metal of group VIII of the Periodic Table and at least one metal capable of alloying with the group VIII noble metal, admixed with a component comprising at least one of the metals rhenium, tungsten or molybdenum. Although it has been claimed therein that improved selectivity to alcohols are achieved over the prior art references it was still reported that 3 to 9 percent of alkanes, such as methane and ethane are formed as by-products during the hydrogenation of acetic acid to ethanol under their optimal catalyst conditions.

U.S. Pat. No. 4,777,303 describes a process for the productions of alcohols by the hydrogenation of carboxylic acids. The catalyst used in this case is a heterogeneous catalyst comprising a first component which is either molybdenum or tungsten and a second component which is a noble metal of Group VIII of the Periodic Table of the elements, optionally on a support, for example, a high surface area graphitized carbon. The selectivity to a combined mixture of alcohol and ester is reported to be only in the range of about 73 to 87 percent with low conversion of carboxylic acids at about 16 to 58 percent. In addition, no specific example of conversion of acetic acid to ethanol is provided.

U.S. Pat. No. 4,804,791 describes another process for the productions of alcohols by the hydrogenation of carboxylic acids. In this process, ethanol is produced from acetic acid or propanol is produced from propionic acid by contacting either acetic acid or propionic acid in the vapor phase with hydrogen at elevated temperature and a pressure in the range from 1 to 150 bar in the presence of a catalyst comprising as essential components (i) a noble metal of Group VIII of the Periodic Table of the elements, and (ii) rhenium, optionally on a support, for example a high surface area graphitized carbon. The conversion of acetic acid to ethanol ranged from 0.6% to 69% with selectivity to ethanol was in the range of about 6% to 97%.

U.S. Pub. No. 2010/0280287 describes a method and compositions for the chemical conversion of syngas to alcohols, wherein the compositions generally include cobalt, molybdenum, and sulfur. This reference further discloses that carbide formation in molybdenum catalysts is not favorable and should be avoided when alcohols are desired products. Furthermore, this reference discloses that molybdenum carbides tend to reduce ethanol selectivity and increase methane selectivity at process conditions suitable for ethanol synthesis.

From the foregoing it is apparent that the need remains for processes and catalysts having a desirable selectivity to ethanol and employing active phases that are readily available and generally inexpensive.

SUMMARY OF THE INVENTION

In a first embodiment, the present invention is directed to a process for selective and direct formation of ethanol from acetic acid comprising contacting a feed stream comprising acetic acid and hydrogen in vapor form at an elevated temperature with a hydrogenation catalyst comprising molybdenum carbide and one or more promoter metals selected from the group consisting of copper, iron, cobalt, nickel, ruthenium, rhodium, palladium, osmium, iridium, platinum, titanium, zinc, chromium, rhenium, potassium, tin and tungsten, on a catalyst support.

In a second embodiment, the present invention is directed to a process for selective and direct formation of ethanol from acetic acid comprising contacting a feed stream comprising acetic acid and hydrogen in vapor form at an elevated temperature with a hydrogenation catalyst comprising molybdenum carbide and one or more promoter metals selected from the group consisting of copper, palladium, and platinum on a catalyst support.

DETAILED DESCRIPTION OF THE INVENTION

The present invention relates to processes and catalysts for use in processes for producing ethanol by hydrogenating acetic acid in the presence of a catalyst. The catalyst employed comprises molybdenum carbide (Mo$_2$C) and one or more promoter metals selected from the group consisting of copper, iron, cobalt, nickel, ruthenium, rhodium, palladium, osmium, iridium, platinum, titanium, zinc, chromium, rhenium, potassium, tin and tungsten, supported on a catalyst support.

The hydrogenation of acetic acid to form ethanol may be represented by the following reaction:

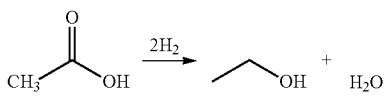

It has surprisingly and unexpectedly been discovered that the catalysts of the present invention provide high selectivities to ethoxylates, such as ethanol and ethyl acetate, and in particular to ethanol, when employed in the hydrogenation of acetic acid. Embodiments of the present invention beneficially may be used in industrial applications to produce ethanol on an economically feasible scale.

The catalyst of the invention comprises molybdenum carbide and one or more promoter metals on a support. Molybdenum carbide exists in many crystalline forms, the most common of which are α-Mo$_2$C and β-Mo$_2$C. Both α-Mo$_2$C and β-Mo$_2$C forms of molybdenum carbide are suitable for the processes of the present invention. As indicated above, the promoter metal may be selected from copper, iron, cobalt, nickel, ruthenium, rhodium, palladium, osmium, iridium, platinum, titanium, zinc, chromium, rhenium, potassium, tin or tungsten. In a preferred embodiment, the promoter metal is copper, platinum or palladium. In some embodiments, the catalyst may employ one of these promoter metals and one or more additional metals, which may or may not be selected from the aforementioned list of promoter metals. For example, the catalyst may include one of the listed promoter metals, two of the listed promoter metals, or three or more of the listed promoter metals.

In some embodiments, molybdenum carbide is present in the catalyst preferably is from 0.1 to 25 wt. %, e.g., from 0.1 to 15 wt. %, from 0.1 wt. % to 10 wt. % or from 0.5 to 5.0 wt. %, and the promoter metal is present in an amount from 0.1 and 20 wt. %, e.g., from 0.1 to 10 wt. %, from 0.1 to 5 wt. % or 0.1 to 2.5 wt. %. For purposes of the present specification, unless otherwise indicated, weight percent is based on the total weight of the catalyst including metal and support. The promoter metal(s) in the catalyst may be present in elemental form or in the form of one or more metal oxides. For purposes of determining the weight percent of the metal(s) in the catalyst, the weight of any oxygen that is bound to the metal is ignored, although the weight of the oxygen is factored in the total weight of the catalyst. For convenience, the present specification refers to the molybdenum carbide as the primary catalyst and any additional metals as promoter metals. This should not be taken as an indication of the underlying mechanism of the catalytic activity. The metals may be alloyed with one another or may comprise a non-alloyed metal solution or mixture.

In some embodiments, a catalyst of the present invention comprises molybdenum carbide and one or more promoter metals in a mole ratio of the molybdenum carbide to the one or more promoter metals from 50:1 to 1:10, e.g., from 20:1 to 1:4, or from 10:1 to 1:2.

In one embodiment, the catalyst comprises from 0.5 to 10 wt. % molybdenum carbide and 0.1 to 2.5 wt. % palladium or platinum. In another embodiment, the catalyst comprises from 0.5 to 10 wt. % molybdenum carbide and 0.1 to 5 wt. % copper.

Depending primarily on how the catalyst is manufactured, the metals of the catalysts of the present invention may be dispersed throughout the support, coated on the outer surface of the support (egg shell) or decorated on the surface of the support.

In addition to molybdenum carbide and one or more promoter metals, the catalyst of the present invention further comprises a suitable support. As will be appreciated by those of ordinary skill in the art, the support materials should be selected such that the catalyst system is suitably active, selective and robust under the process conditions employed for the formation of ethanol. Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica and mixtures thereof. Other supports may be used in some embodiments of the present invention, including without limitation, alumina, metasilicate, carbon, zirconia, titania, magnesium oxide, iron oxide, yttria, and zeolite, and mixtures thereof.

In some embodiments, the support comprises a support modifier, such as an acidic or basic modifier, having a low volatility or that is non-volatile. Low volatility modifiers have a rate of loss that is low enough such that the acidity of the support modifier is not reversed during the life of the catalyst.

In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Exemplary acidic support modifiers include those selected from the group consisting of TiO$_2$, ZrO$_2$, Nb$_2$O$_5$, Ta$_2$O$_5$, Al$_2$O$_3$, B$_2$O$_3$, P$_2$O$_5$, and Sb$_2$O$_3$. Preferred acidic support modifiers include those selected from the group consisting of TiO$_2$, ZrO$_2$, Nb$_2$O$_5$, Ta$_2$O$_5$, and Al$_2$O$_3$. The acidic modifier may also include WO$_3$, MoO$_3$, Fe$_2$O$_3$, Cr$_2$O$_3$, V$_2$O$_5$, MnO$_2$, CuO, Co$_2$O$_3$, Bi$_2$O$_3$.

Suitable basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used in embodiments of the present invention. Preferably, the support modifier is selected from the group consisting of oxides and metasilicates of any of sodium, potassium, magnesium, calcium, scandium, yttrium, and zinc, and mixtures of any of the foregoing. Preferably, the support modifier is a calcium silicate, more preferably calcium metasilicate (CaSiO$_3$). If the support modifier comprises calcium metasilicate, it is preferred that at least a portion of the calcium metasilicate is in crystalline form.

The total weight of the modified support, which includes the support material and the support modifier, based on the total weight of the catalyst, preferably is from 75 wt. % to 99.9 wt. %, e.g., from 78 wt. % to 97 wt. %, or from 80 wt. % to 95 wt. %. The support modifier preferably is provided in an amount sufficient to adjust the acidity of the overall catalyst. For example, for basic modifiers the amount of support modifier preferably is sufficient to reduce the number or reduce the availability of active Brønsted acid sites, and more preferably to ensure that the surface of the support is substantially free of active Brønsted acid sites. In some embodiments, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst. In some embodiments, the support material may be present in an amount from 25 wt. % to 99 wt. %, e.g., from 30 wt. % to 97 wt. % or from 35 wt. % to 95 wt. %.

In one embodiment, the support material is a silicaceous support material selected from the group consisting of silica, silica/alumina, a Group IIA silicate such as calcium metasilicate, pyrogenic silica, high purity silica and mixtures thereof. In the case where silica is used as the silicaceous support, it is beneficial to ensure that the amount of aluminum, which is a common contaminant for silica, is low, preferably under 1 wt. %, e.g., under 0.5 wt. % or under 0.3 wt. %, based on the total weight of the modified support. In this regard, pyrogenic silica is preferred as it commonly is available in purities exceeding 99.7 wt. %. High purity silica, as used throughout the application, refers to silica in which acidic contaminants such as aluminum are present, if at all, at levels of less than 0.3 wt. %, e.g., less than 0.2 wt. % or less than 0.1 wt. %. When calcium metasilicate is used as a support modifier, it is not necessary to be quite as strict about the purity of the silica used as the support material although aluminum remains undesirable and will not normally be added intentionally. The aluminum content of such silica, for example, may be less than 10 wt. %, e.g., less than 5 wt. % or less than 3 wt. %. In cases where the support comprises a support modifier in the range of from 2 wt. % to 10 wt. %, larger amount of acidic impurities, such as aluminum, can be tolerated so long as they are substantially counter-balanced by an appropriate amount of a support modifier.

The surface area of the silicaceous support material, e.g., silica, preferably is at least about 50 $m^2/g$, e.g., at least about 100 $m^2/g$, at least about 150 $m^2/g$, at least about 200 $m^2/g$ or most preferably at least about 250 $m^2/g$. In terms of ranges, the silicaceous support material, e.g., silica, preferably has a surface area of from 50 to 600 $m^2/g$, e.g., from 100 to 500 $m^2/g$ or from 100 to 300 $m^2/g$. High surface area silica, as used throughout the application, refers to silica having a surface area of at least about 250 $m^2/g$. For purposes of the present specification, surface area refers to BET nitrogen surface area, meaning the surface area as determined by ASTM D6556-04, the entirety of which is incorporated herein by reference.

The silicaceous support material also preferably has an average pore diameter of from 5 to 100 nm, e.g., from 5 to 30 nm, from 5 to 25 nm or from about 5 to 10 nm, as determined by mercury intrusion porosimetry, and an average pore volume of from 0.5 to 2.0 $cm^3/g$, e.g., from 0.7 to 1.5 $cm^3/g$ or from about 0.8 to 1.3 $cm^3/g$, as determined by mercury intrusion porosimetry.

The morphology of the support material, and hence of the resulting catalyst composition, may vary widely. In some exemplary embodiments, the morphology of the support material and/or of the catalyst composition may be pellets, extrudates, spheres, spray dried microspheres, rings, pentarings, trilobes, quadrilobes, multi-lobal shapes, or flakes although cylindrical pellets are preferred. Preferably, the silicaceous support material has a morphology that allows for a packing density of from 0.1 to 1.0 $g/cm^3$, e.g., from 0.2 to 0.9 $g/cm^3$ or from 0.5 to 0.8 $g/cm^3$. In terms of size, the silica support material preferably has an average particle size, e.g., meaning the diameter for spherical particles or equivalent spherical diameter for non-spherical particles, of from 0.01 to 1.0 cm, e.g., from 0.1 to 0.5 cm or from 0.2 to 0.4 cm. Since the one or more metal(s) that are disposed on or within the modified support are generally very small in size, they should not substantially impact the size of the overall catalyst particles. Thus, the above particle sizes generally apply to both the size of the modified supports as well as to the final catalyst particles.

A preferred silica support material is SS61138 High Surface Area (HSA) Silica Catalyst Carrier from Saint Gobain N or Pro. The Saint-Gobain N or Pro SS61138 silica contains approximately 95 wt. % high surface area silica; a surface area of about 250 $m^2/g$; a median pore diameter of about 12 nm; an average pore volume of about 1.0 $cm^3/g$ as measured by mercury intrusion porosimetry and a packing density of about 0.352 $g/cm^3$ (22 $lb/ft^3$).

A preferred silica/alumina support material is KA-160 (Sud Chemie) silica spheres having a nominal diameter of about 5 mm, a density of about 0.562 g/ml, an absorptivity of about 0.583 g $H_2O$/g support, a surface area of about 160 to 175 $m^2/g$, and a pore volume of about 0.68 ml/g.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744 and 7,863,489 and U.S. Pub. No. 2010/0197485, the entireties of which are incorporated herein by reference.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments, a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 40 mole % of the converted acetic acid is converted to ethanol, we refer to the ethanol selectivity as 40%. Preferably, the catalyst selectivity to ethoxylates is at least 40%, e.g., at least 50%, or at least 60%. As used herein, the term "ethoxylates" refers specifically to the compounds ethanol, acetaldehyde, and ethyl acetate. Preferably, the selectivity to ethanol is at least 40%, e.g., at least 50%, or at least 60%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 200 grams of ethanol per kilogram catalyst per hour, e.g., at least 400 grams of ethanol per kilogram catalyst per hour, or at least 600 grams of ethanol per kilogram catalyst per hour, is preferred. In terms of ranges, the productivity preferably is from 200 to 3,000 grams of ethanol per kilogram catalyst per hour, e.g., from 400 to 2,500 grams of ethanol per kilogram catalyst per hour or from 600 to 2,000 grams of ethanol per kilogram catalyst per hour.

The hydrogenation of acetic acid to form ethanol may be carried out in the vapor or liquid form under a wide variety of conditions. Preferably, the reaction is carried out in the vapor form. Reaction temperatures may be employed, for example in the range from 125° C. to 350° C., e.g., from 200° C. to 325° C., from 225° C. to 300° C., or from 250° C. to 300° C. The reaction may be conducted at subatmospheric, atmospheric or superatmospheric pressures. Without being bound to any particular theory, operating the reaction at higher pressures increases the ethanol selectivity of a catalyst comprising molybdenum carbide and a promoter metal. In some embodiments, the pressure may range from 10 KPa to 3000 KPa, e.g., from 50 KPa to 2300 KPa, or from 100 KPa to 1500 KPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $hr^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

Although the reaction consumes two moles of hydrogen per mole of acetic acid to produce a mole of ethanol, the actual molar ratio of acetic acid to hydrogen in the feed stream may be varied between wide limits, e.g., from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

The raw materials used in connection with the process of this invention may be derived from any suitable source including natural gas, petroleum, coal, biomass and so forth. It is well known to produce acetic acid through methanol carbonylation, acetaldehyde oxidation, ethylene oxidation, oxidative fermentation, and anaerobic fermentation and so forth. As petroleum and natural gas have become more expensive, methods for producing acetic acid and intermediates such as methanol and carbon monoxide from alternate carbon sources have drawn more interest. Of particular interest is the production of acetic acid from synthesis gas (syngas) that may be derived from any suitable carbon source. U.S. Pat. No. 6,232,352 the disclosure of which is incorporated herein by reference, for example, teaches a method of retrofitting a methanol plant for the manufacture of acetic acid. By retrofitting a methanol plant the large capital costs associated with CO generation for a new acetic acid plant are significantly reduced or largely eliminated. All or part of the syngas is diverted from the methanol synthesis loop and supplied to a separator unit to recover CO and hydrogen, which are then used to produce acetic acid. In a similar manner, hydrogen for the hydrogenation step may be supplied from syngas.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form syngas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

In some embodiments, some or all of the raw materials for the above-described acetic acid hydrogenation process may be derived partially or entirely from syngas. For example, the acetic acid may be formed from methanol and carbon monoxide, both of which may be derived from syngas. For example, the methanol may be formed by steam reforming syngas, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof.

The acetic acid may be vaporized at the reaction temperature, and then it can be fed along with hydrogen in undiluted state or diluted with a relatively inert carrier gas, such as nitrogen, argon, helium, carbon dioxide and the like.

Alternatively, acetic acid in vapor form may be taken directly as crude product from the flash vessel of a methanol carbonylation unit of the class described in U.S. Pat. No. 6,657,078, the disclosure of which is incorporated herein by reference. The crude vapor product may be fed directly to the reaction zones of the present invention without the need for condensing the acetic acid and light ends or removing water, saving overall processing costs.

The acetic acid fed to the hydrogenation reaction may also comprise other carboxylic acids and anhydrides, as well as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

Contact or residence time can also vary widely, depending upon such variables as amount of acetic acid, catalyst, reactor, temperature and pressure. Typical contact times range from a fraction of a second to more than several hours when a catalyst system other than a fixed bed is used, with preferred contact times, at least for vapor phase reactions, between about 0.5 and 100 seconds.

Some embodiments of the process of hydrogenating acetic acid to form ethanol according to one embodiment of the invention may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

Typically, the catalyst is employed in a fixed bed reactor, e.g., in the shape of an elongated pipe or tube where the reactants, typically in the vapor form, are passed over or through the catalyst. Other reactors, such as fluid or ebullient bed reactors, can be employed, if desired. In some instances, it is advantageous to use the hydrogenation catalysts in conjunction with an inert material to regulate the pressure drop, flow, heat balance or other process parameters in the catalyst bed including the contact time of the reactant compounds with the catalyst particles.

Operating under the conditions of the present invention may have an ethanol production on the order of at least 0.1 tons of ethanol per hour, at least 5 tons of ethanol per house, or preferably at least 5 tons of ethanol per hour. Large scale industrial production of ethanol, depending on the scale, generally should be at least 15 tons of ethanol per hour, preferably at least 30 tons of ethanol per hour. In terms of ranges for large scale industrial production of ethanol, the process of the present invention may produce 15 to 160 tons of ethanol per hour, preferably 30 to 80 tons of ethanol per hour. Ethanol production from fermentation, due the economies of scale, typically does not permit large scale ethanol production in one facility that may be achievable by embodiments of the present invention.

In various embodiments of the present invention, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 35 wt. % water. In some embodiments, the crude ethanol product comprises ethanol in an amount from 5 wt. % to 70 wt. %, e.g., from 10 wt. % to 60 wt. %, or from 15 wt. % to 50 wt. %, based on the total weight of the crude ethanol product. Preferably, the crude ethanol product contains at least 10 wt. % ethanol, at least 15 wt. % ethanol or at least 20 wt. % ethanol. The crude ethanol product typically will further comprise unreacted acetic acid, depending on conversion, for example, in an amount of less than 90 wt. %, e.g., less than 80 wt. % or less than 70 wt. %. In terms of ranges, the unreacted acetic acid is preferably from 0 to 90 wt. %, e.g., from 5 to 80 wt. %, from 15 to 70 wt. %, from 20 to 70 wt. % or from 25 to 65 wt. %. As water is formed in the reaction process, water will be present in the crude ethanol product, for example, in amounts ranging from 5 to 35 wt. %, e.g., from 10 to 30 wt. % or from 10 to 26 wt. %.

Ethyl acetate may also be produced during the hydrogenation of acetic acid, or through side reactions and may be present, for example, in amounts ranging from 0 to 20 wt. %, e.g., from 0 to 15 wt. %, from 1 to 12 wt. % or from 3 to 10 wt. %. In addition, acetaldehyde may be produced through side reactions, and may be present, for example, in the crude ethanol product in amounts ranging from 0 to 10 wt. %, e.g., from 0 to 3 wt. %, from 0.1 to 3 wt. % or from 0.2 to 2 wt. %. Other components, such as, for example, esters, ethers, aldehydes, ketones, alkanes, and carbon dioxide, if detectable, collectively may be present in amounts less than 10 wt. %, e.g., less than 6 wt. % or less than 4 wt. %. In terms of ranges, these other components may be present in an amount from 0.1 to 10 wt. %, e.g., from 0.1 to 6 wt. %, or from 0.1 to 4 wt. %. Exemplary component ranges for the crude ethanol product are provided in Table 1.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 10 to 60 | 15 to 50 | 25 to 50 |
| Acetic Acid | 0 to 90 | 5 to 80 | 15 to 70 | 20 to 70 |
| Water | 5 to 35 | 5 to 30 | 10 to 30 | 10 to 26 |
| Ethyl Acetate | 0 to 20 | 0 to 15 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

Ethanol may be recovered from the crude ethanol product using one or more distillation columns. The final ethanol product produced by the process of the present invention may be an industrial grade ethanol comprising from 75 to 96 wt. % ethanol, e.g., from 80 to 96 wt. % or from 85 to 96 wt. % ethanol, based on the total weight of the ethanol product. Exemplary finished ethanol compositional ranges are provided below in Table 2.

TABLE 2

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 2, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircrafts. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, the following examples are provided below. It should be understood that these examples are for illustrative purposes only and is not to be construed as limiting the invention in any manner.

EXAMPLES

Example 1

In a tubular reactor made of stainless steel, having an internal diameter of 30 mm and capable of being raised to a controlled temperature, a catalyst was arranged comprising 8 wt. % molybdenum carbide and 5 wt. % copper on silica. The length of the catalyst bed after charging was approximately 70 mm.

A feed liquid of acetic acid was evaporated and charged to the reactor along with hydrogen and helium as a carrier gas with an average combined gas hourly space velocity (GHSV) of about 2500 hr$^{-1}$ at a temperature of about 250° C. and pressure of 14 barg. The molybdenum carbide and copper catalyst demonstrated a selectivity to ethoxylates of 98.9%. The selectivity to ethane was 1.5%.

Example 2

The reactor and procedure of Example 1 was repeated, except with a catalyst comprising 8 wt. % molybdenum carbide and 1 wt. % palladium on silica.

A feed liquid of acetic acid was evaporated and charged to the reactor along with hydrogen and helium as a carrier gas with an average combined gas hourly space velocity (GHSV) of about 2500 hr$^{-1}$ at a temperature of about 250° C. and pressure of 14 barg. The selectivity to ethanol was 64.4% at a conversion of acetic acid of 52.5%. The selectivity to ethoxylates was 98.3%. The selectivity to ethane was 1.7%.

Example 3

The reactor and procedure of Example 1 was repeated, except with a catalyst comprising 8 wt. % molybdenum carbide and 1 wt. % palladium on silica.

A feed liquid of acetic acid was evaporated and charged to the reactor along with hydrogen and helium as a carrier gas with an average combined gas hourly space velocity (GHSV) of about 2500 hr$^{-4}$ at a temperature of about 250° C. and pressure of 14 barg. The selectivity to ethanol was 64.5% with a conversion of acetic acid of 62%. The selectivity to ethoxylates was 98.3%. The selectivity to ethane was 1.7%.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art.

We claim:

1. A process for selective and direct formation of ethanol from acetic acid comprising:
contacting a feed stream comprising acetic acid and hydrogen in vapor form at an elevated temperature with a hydrogenation catalyst comprising molybdenum carbide and one or more promoter metals selected from the group consisting of copper, iron, cobalt, nickel, ruthenium, rhodium, palladium, osmium, iridium, platinum, titanium, zinc, chromium, rhenium, potassium, tin and tungsten, on a catalyst support.

2. The process of claim 1, wherein the catalyst support is selected from the group consisting of silica, silica/alumina, calcium metasilicate, pyrogenic silica, high purity silica and mixtures thereof.

3. The process of claim 1, wherein the loading of molybdenum carbide is from 0.1 wt. % to 25 wt. %.

4. The process of claim 1, wherein the loading of promoter metal is from 0.1 wt. % to 20 wt. %.

5. The process of claim 1, wherein the promoter metal comprises copper.

6. The process of claim 5, wherein the loading of molybdenum carbide is from 0.5 to 10 wt. % and the loading of copper is from 0.1 to 5 wt. %.

7. The process of claim 1, wherein the promoter metal comprises palladium or platinum.

8. The process of claim 7, wherein the loading of molybdenum is from 0.5 to 10 wt. % and the loading of palladium is from 0.1 to 2.5 wt. %.

9. The process of claim 1, wherein the process yields an acetic acid conversion of at least 10%.

10. The process of claim 1, wherein the hydrogenation catalyst has a selectivity to ethanol of at least 40%.

11. The process of claim 1, wherein the hydrogenation catalyst has a selectivity to methane, ethane, and carbon dioxide of less than 4%.

12. The process of claim 1, wherein the hydrogentation catalyst has a selectivity to ethoxylates of at least 40%.

13. The process of claim 1, wherein the hydrogenation of acetic acid is carried out at a temperature of 125° C. to 350° C.

14. The process of claim 1, wherein the hydrogenation of acetic acid is carried out at a pressure of 10 KPa to 3000 KPa.

15. The process of claim 1, wherein the hydrogenation catalyst further comprises a support modifier.

16. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

* * * * *